US012714591B2

(12) United States Patent
Greenfield

(10) Patent No.: US 12,714,591 B2
(45) Date of Patent: Aug. 25, 2026

(54) SUPPORT STRAP FOR A KNEE IMMOBILIZING SPLINT

(71) Applicant: Brian Greenfield, Quebec (CA)

(72) Inventor: Brian Greenfield, Quebec (CA)

(73) Assignee: Brian Greenfield, Quebec (CA)

( * ) Notice: Subject to any disclaimer, the term of this patent is extended or adjusted under 35 U.S.C. 154(b) by 591 days.

(21) Appl. No.: 17/736,958

(22) Filed: May 4, 2022

(65) Prior Publication Data

US 2023/0355419 A1 Nov. 9, 2023

(51) Int. Cl.
*A61F 5/058* (2006.01)

(52) U.S. Cl.
CPC .................................. *A61F 5/0585* (2013.01)

(58) Field of Classification Search
CPC .... A61F 5/0123; A61F 5/0193; A61F 5/3715; A61F 5/0106; A61F 5/0109; A61F 5/26; A61F 5/3776; A61F 5/3784; A61F 5/4408; A61F 5/447; A61F 2007/0228; A61F 13/64; A61F 13/66; A45F 3/005; A45F 3/14
See application file for complete search history.

(56) References Cited

U.S. PATENT DOCUMENTS 1,965,314 A * 7/1934 Henderson ............. A41B 11/12 450/111
2,460,895 A * 2/1949 Meany .................. A61F 5/0123 403/62
3,307,872 A * 3/1967 Murcott ................. A61G 1/044 297/468
3,528,412 A * 9/1970 Mcdavid ............... A61F 5/0125 2/22
3,947,927 A * 4/1976 Rosenthal ............ A63C 11/025 24/298
4,598,702 A * 7/1986 Lilla ..................... A61F 5/3738 602/4
4,913,136 A * 4/1990 Chong .................. A61F 5/0193 602/24
5,139,476 A * 8/1992 Peters ................... A61F 5/0106 602/26
5,236,411 A * 8/1993 Backman .............. A61F 5/3753 128/DIG. 20
5,286,251 A * 2/1994 Thompson ............ A61F 5/0193 128/99.1

(Continued)

OTHER PUBLICATIONS

International Search Report and Written Opinion in corresponding International Application No. PCT/US2023/020910 mailed Aug. 31, 2023, 10 pages.

(Continued)

*Primary Examiner* — Kari K Rodriquez
(74) *Attorney, Agent, or Firm* — Leason Ellis LLP

(57) ABSTRACT

A support strap for a knee immobilizing splint with a segment along its length to receive the knee of a wearer. The strap has a hook fixed to a first end that engages an upper part of the splint. The other end of the strap has a connection assembly for attaching the strap to a belt of a wearer so the belt and hook are fixed at a certain distance from each other. This distance is such that the splint is held so the knee of the wearer is at the knee segment of the splint and the splint is prevented from sliding down the leg of the wearer while standing or walking.

3 Claims, 6 Drawing Sheets

(56) References Cited

U.S. PATENT DOCUMENTS

| | | | | |
|---|---|---|---|---|
| 5,829,443 | A * | 11/1998 | Cunningham | A61F 5/3715 128/869 |
| 6,095,993 | A * | 8/2000 | Hawkins | A61F 5/3738 602/4 |
| 6,428,495 | B1 * | 8/2002 | Lynott | A61F 5/3715 602/23 |
| 6,979,303 | B2 * | 12/2005 | Jestrabek-Hart | A61F 5/3738 2/45 |
| 8,628,488 | B2 * | 1/2014 | Serola | A61H 1/00 2/338 |
| 8,945,032 | B2 * | 2/2015 | Nevels | A61F 5/0123 2/338 |
| 9,788,976 | B1 | 10/2017 | Thompson | |
| 2004/0181852 | A1 * | 9/2004 | Cogswell | A61F 5/3715 2/313 |
| 2006/0124162 | A1 | 6/2006 | Sweeney | |
| 2011/0089204 | A1 * | 4/2011 | Escalante | A45F 5/00 224/148.3 |
| 2012/0330203 | A1 * | 12/2012 | Jones | A61F 5/0123 602/16 |
| 2015/0032040 | A1 * | 1/2015 | Cadichon | A61F 5/3715 602/19 |
| 2017/0367866 | A1 | 12/2017 | Robinson | |
| 2020/0375774 | A1 | 12/2020 | Balentine | |
| 2021/0137718 | A1 * | 5/2021 | Faloon | A61F 5/0125 |
| 2024/0058155 | A1 * | 2/2024 | Perez | A61F 5/3715 |

OTHER PUBLICATIONS

Nvorliy ROM Knee Brace with Shoulder Strap, Post Op Hinged Immobilizer Support, Recovery Stabilization for AGL, PCL, MCL, Oste Arthritis, Joint Injuries and Orthopedic Rehab. Amazon. Apr. 19, 2021 (Apr. 19, 2021 ). [Retrieved on Jul. 16, 2021]. Retrieved from the fnternet:<URL: https://www.amazon.com/Nvorliy-Immobilizer-Stabilization-Arthritis-Orthopedic/dp/B092W7CN3H?th=1>entire document, 5 pages.

* cited by examiner

SUPPORT STRAP FOR A KNEE IMMOBILIZING SPLINT

FIELD OF THE INVENTION

The present invention relates generally to apparatus for stabilizing the thigh and lower leg of a patient after an injury in order to help assure proper healing and, more particularly, to a splint for stabilizing the thigh and lower leg of a user with respect to each other, while preventing the splint from sliding down the leg of the user while walking.

BACKGROUND OF THE INVENTION

The purpose of a knee immobilizing splint is to support the healing of the patient's leg by keeping the knee straight. Knee immobilizing splints are designed to prevent the knee from bending for a period of time either before or after knee surgery. They are typically designed with an upper section that is fitted around the thigh of the user and a lower section that fits around the lower leg or calf. A structure holds the upper and lower sections in a relatively fixed position with respect to each other to reduce flexing of the knee.

Attached FIGS. 1 and 3 show a side view and a front view, respectively, of an immobilizing splint 100. Some splints immobilize in such a way that movement at the knee is not permitted. This risks significant knee stiffness. As a result, some of these splints allow for a limited range of hinged movement so that the thigh and calf are generally immobilized with respect to each other, but there is still a range of flexion and extension. This is important for ligamental injuries where the object is to limit valgus and *varus* forces while preventing stiffness of the knee. The suggested range of movement depends on the injury. It is also useful for individuals with tom and injured tendons.

A popular brand of immobilizing splint is the Zimmer splint, and some immobilizing splints are generally known as Zimmer splints, whether made by the Zimmer Biomet company or not. As shown in FIGS. 1-3 the immobilizing splint is a frame for stabilizing a patient's leg with an upper portion 102 located about the upper leg or thigh of the user and a lower portion 104 located about the lower leg or calf of the user. The upper and lower portions are stabilized with respect to each by one or more rods 218 located in pockets 216 toward the back of the splint. The splint can be a one-piece open unit as shown in FIG. 2 that can be wrapped about the leg with its ends fastened together by VELCRO® hook and loop sections and belts that engage hooks fastened to a vertical structure 210. The vertical structure 210 in FIG. 2 is in two pieces, one on each side of the leg. However, a single structure could also be used.

As best seen in FIG. 1 the splint is larger at the top to accommodate the thigh of the user and smaller in the lower portion to fit about the calf of the user. Also, the upper and lower portions may have a tapered shape. Thus, as the patient begins to regain mobility and starts to stand and/or walk, the splint tends to slide down the leg of the user and has to be pulled up repeatedly to keep it in place. Compare the location of the bottom of the splint in FIG. 1 and FIG. 3.

This need to pull up the splint is distracting for the patient and also requires repeated use of the physical strength of the patient to pull up on the splint. If the patient is elderly, they may not have the strength and/or stamina to continue to perform this pulling up procedure. Similarly, if the patient has impaired upper body strength because of an accident in which the leg was injured or otherwise, this pulling up procedure may delay the recovery of the patient's upper arm and torso muscles.

Thus, it would be advantageous if there were a simple and inexpensive device that could act to keep the splint from sliding down the user's leg while the user is standing or walking.

SUMMARY OF THE INVENTION

The present invention is directed to apparatus for stabilizing the thigh and lower leg of a patient after an injury in order to help assure proper healing and, more particularly, to a splint for stabilizing the thigh and lower leg of a user with respect to each other, while preventing the splint from sliding down the leg of the user during standing or walking.

The present invention provides a solution to the problem of needing to pull up the splint by providing a strap that is attached to an upper section or loop of the splint by means of a hook of some type. The strap is then passed over the belt of the user so that the end hangs down next to the rest of the strap and is then held in place, e.g., by VELCRO® hook and loop strips. The strap can have adjustable buckle clasps so its length can be customized for the patient.

Instead of a buckle clasp, the strap can have a relatively long section of VELCRO® hook and loop strip on its end that can be passed over the belt and held in place by contacting another section of VELCRO® hook and loop strip at a select point toward the midpoint of the strap, thus adjusting its overall length. In place of having the strap pass over the user's belt, the upper end of the strap can be provided with a loop and the user's belt can pass through the loop.

Further, if the user normally does not wear a belt, e.g., a women who typically wears a dress or anyone wearing pajamas, a substitute or auxiliary belt can be provided. The support strap can then be attached between the auxiliary belt and the top of the splint. The strap and belt can be constructed separately, or they can be of an integrated one-piece construction.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 7A is a view of an integral one-piece belt and strap assembly according to the present invention attached to an immobilizing splint, while FIG. 7B shows a close up of a strap according to the invention with a loop at its upper end through which the belt of the patient can pass through.

DETAILED DESCRIPTION OF THE INVENTION

Figure 1:
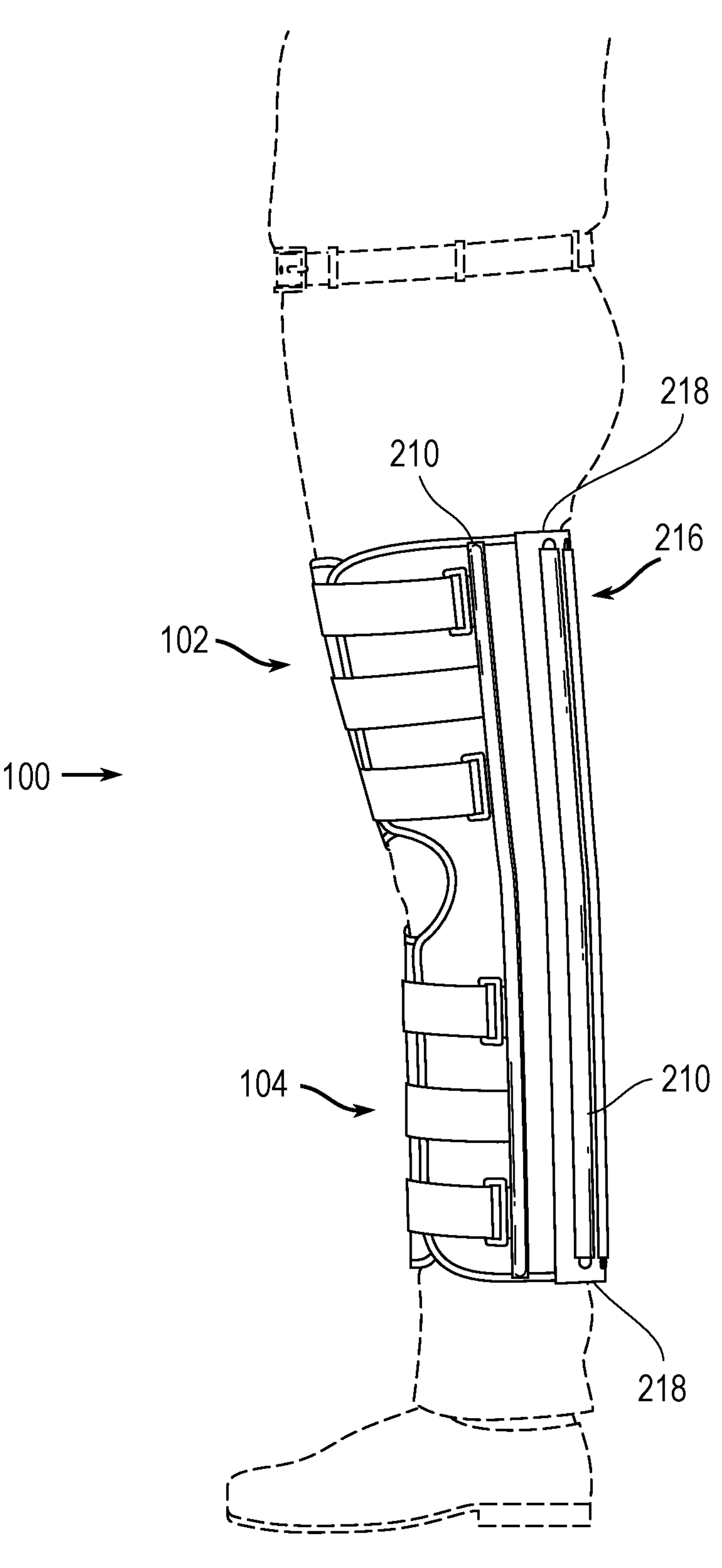
FIG. 1 is a side view of a knee immobilizing splint being wore about the leg of a user or patient.
Figure 2:
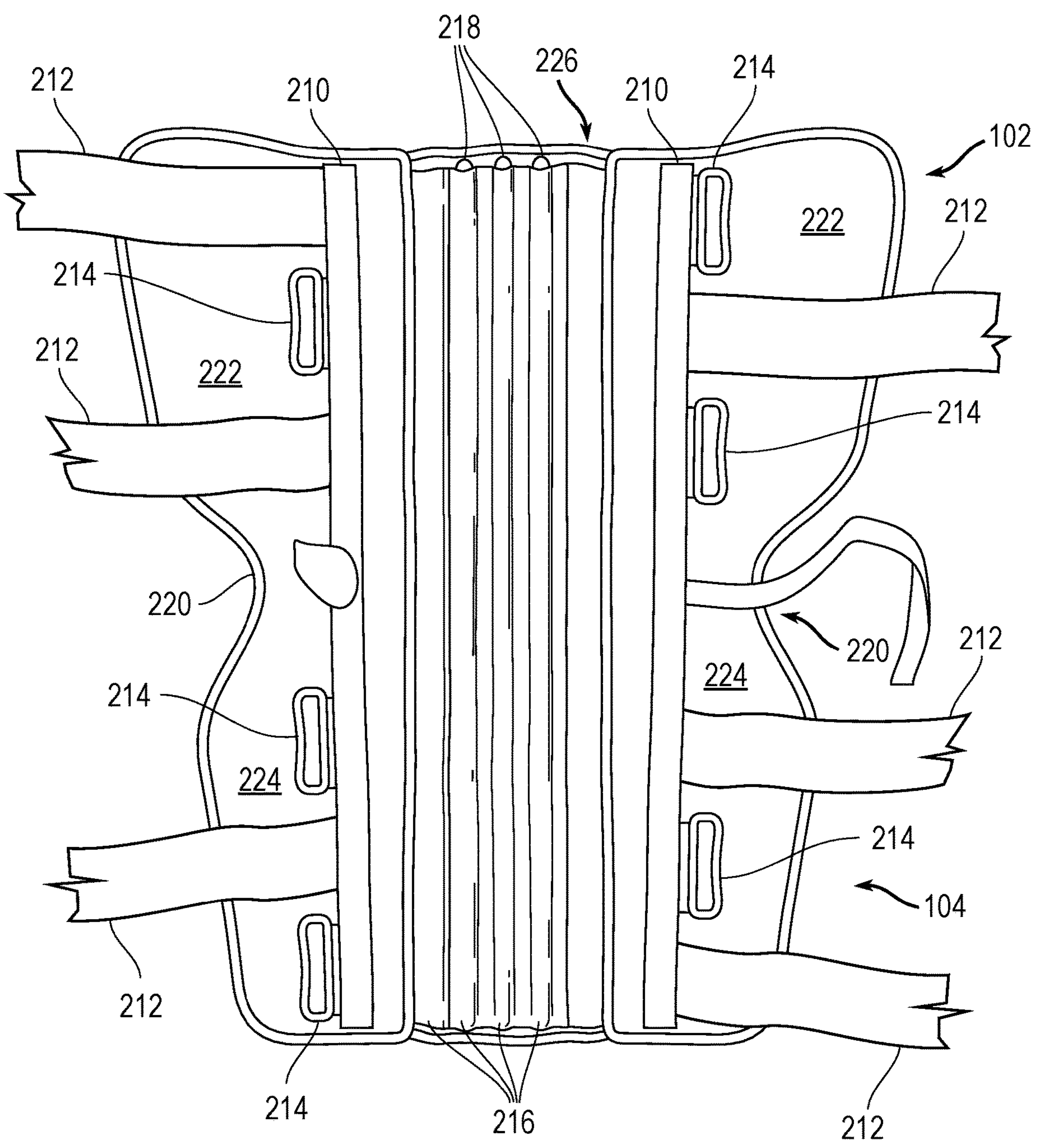
FIG. 2 shows the splint of FIG. 1 prior to being placed about the leg of the patient and in an open splayed position.

FIG. 1 a side view of a knee immobilizing splint, e.g., a Zimmer splint, being wore about their leg of a patient. As can be seen in FIG. 2 the splint is in one-piece and is made primarily of cloth. Its outer perimeter generally tapers inward from top to bottom because the top or upper portion 102 must accommodate the user's thighs and the lower portion 104 only needs to accommodate the user's calf muscles. Vertical strips 210 extend the height of the splint, each being adapted to run along an inner or outer side of the leg. Further, along each vertical strip 210 there are alternating bands 212 and oval loops 214. A generally rectangular center piece 226 extends between the strips 210 and connects tapered upper portions 222 on each side and tapered lower portions 224 on each side. There are large VELCRO® hook and loop panels on the back surfaces (not seen) of portions 222 and 224 so that when the portions 222, 224 are wrapped around the leg of the patient they overlap and can be held in place. Because of the use of VELCRO® hook and loop fasteners the amount of overlap permits widening and narrowing of the brace to accommodate patients with different size thighs.

The oval loops on one strip 210 are aligned with the belts 212 on the other, so that when the splint is wrapped around the leg and held by the VELCRO® hook and loop fastener, it can be further held in place by having the belts extend through the loops.

The rectangular center piece 226 of the splint, which would face the back of the leg of the user, has a series of pockets 216 (e.g., 4) for receiving metal rods 218. These rods immobilize the upper section 102 with respect to the lower section 104 to protect the knee of the user.

Figures 3, 4:
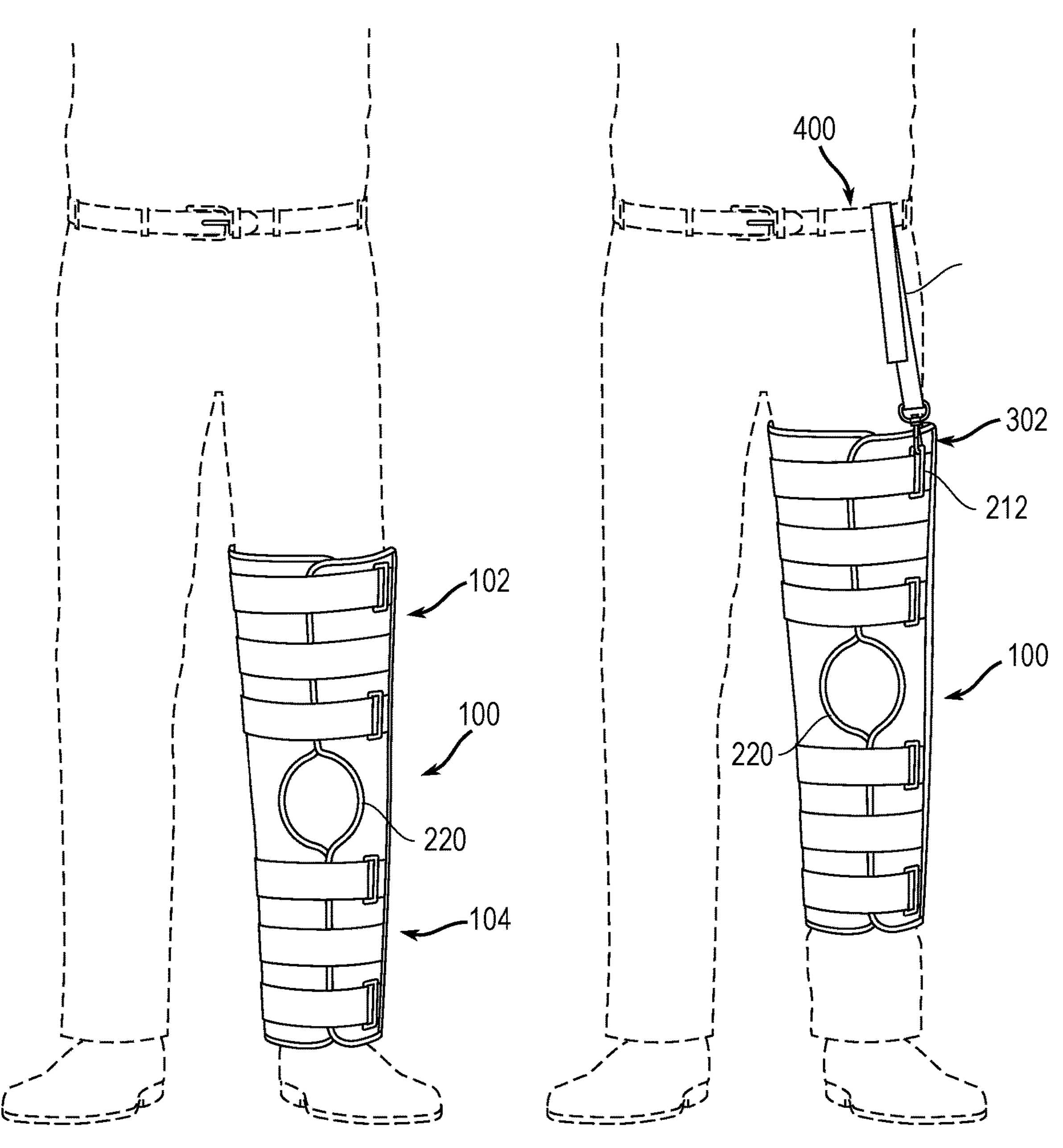
FIG. 3 is a front view of the knee immobilizing splint of FIG. 1 being wore about the leg of a patient and which has slid down the patient's leg.
FIG. 4 is a front view of the knee immobilizing splint of FIGS. 1 and 3 being wore about their leg of a patient, but which is provided with the support strap of the present invention installed between the splint and a belt of the user.

The splint is positioned along the leg of the user so that the knee is located at indents 220 in the perimeter of the splint that separate the upper and lower portions 222, 224. However, as the patient moves about while wearing the splint, it tends to slide down the leg. If unimpeded, it can slide all the way down until its lower edge is resting on the top of the foot, as shown in FIG. 3. If the splint was designed to allow some flexing of the knee, in this position the knee is within the upper section 102 and the knee cannot be flexed.

Figures 5, 6A, 6B:
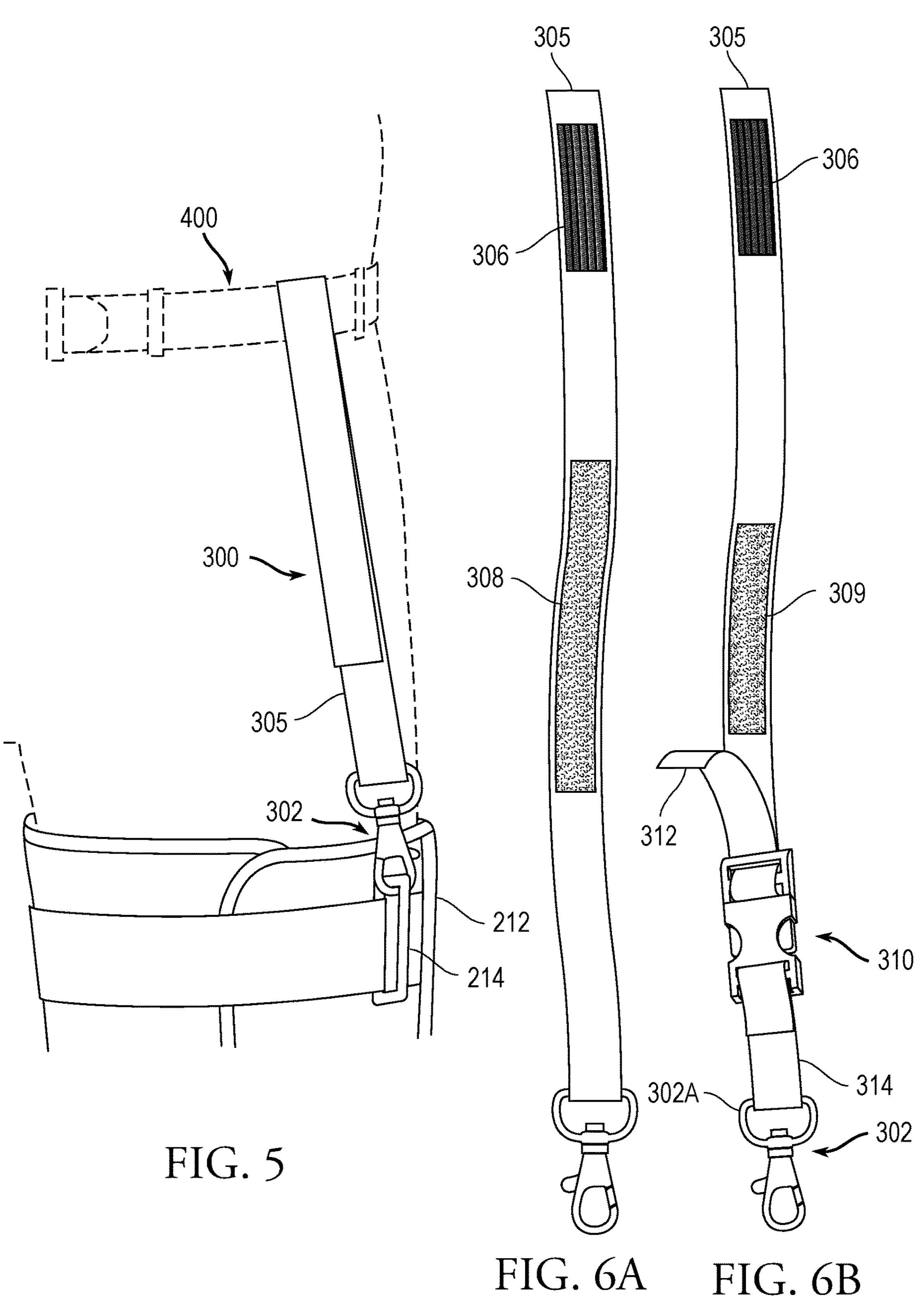
FIG. 5 is a close-up view of FIG. 4 showing the details of an exemplary connection of the strap to the splint.
FIG. 6A is a view of the strap of FIG. 5 detached from the splint and opened so as to view its VELCRO® hook and loop strips for adjusting its overall length from the belt and FIG. 6B is a view of an alternative belt with an exemplary buckle clasp for adjusting its length.

FIG. 4 shows the support strap 300 of the present invention. It can be made of cloth, webbing leather or similar material. As can be seen, it is secured to the user's belt 400 and extends to a hook 302 that is clipped onto one of the loops 214 at the top of the splint. The hook 302 is better seen in FIG. 5. In the embodiment of FIG. 5 one end of the strap is sewn or otherwise attached to the hook 302. The connection shown in FIG. 5 is only illustrative of the present invention and any convenient connection between the strap and the splint can be used. The other end 305 of the strap is passed over the patient's belt 400. There is a VELCRO® hook and loop strip 306 toward the end 305 and a much longer strip 308 toward the middle of the strap. The length of the strap from the belt to the hook 203 is determined by where VELCRO® hook and loop strips 306, 308 are brought into contact with each other. As is clear, strips 306, 308 could be one continuous strip.

Figure 8:
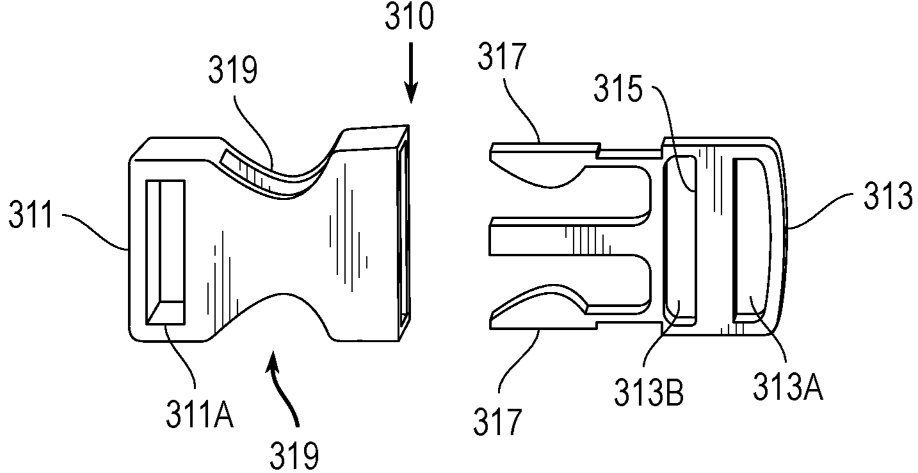
FIG. 8 is a perspective view of the parts of an exemplary buckle clasp.

As an alternative, the strap of FIG. 6B can be substituted for the strap of FIG. 6A. When the strap of FIG. 6B is used, the end 305 is passed over the belt and brought into contact with VELCRO® hook and loop strip 309. Strip 309 can be made shorter than strip 308 in the embodiment of FIG. 6A because it does need to be as adjustable as in FIG. 6A. This is because the strap of FIG. 6B includes an adjustable buckle clasp 310. A typical adjustable buckle clasp is shown in FIG. 8. It has a male part 313 that is connected to the end of the strap away from the VELCRO® hook and loop strips. In FIG. 8 the end 312 would enter a retainer slot 313B from the rear right, loop about center post 315, pass into the retainer slot 313A and extend back to the right adjacent the earlier section of strap. Friction between the strap and the center bar as well as between the two overlaying sections of the strap hold the male part 313. A short strap 314 (FIG. 6B) is sewn to a loop 302A of the hook 302 and to a slot 311A of the female part 311 of the buckle clasp. The male part 313 has flexible prongs 317 that are compressed as the male part is inserted into the female part and which expand into openings 319 in the female part to hold the two parts of the buckle clasp together. In other words, the short strap 314 is securely fastened between one end of buckle clasp 310 and the hook 302. By pulling on end 312 of the section of strap as shown in FIG. 6B that connects to the buckle clasp 310, the strap can be shortened in length.

Further, the buckle clasps is likely to be able to hold with more tension than just connected VELCRO® hook and loop strips. In order to take advantage of this, a buckle clasp can be substituted for the connected Velcro® strips.

In FIG. 7 there is shown an arrangement with a strap like that of FIG. 6B, except that the end 305 is sewn onto an auxiliary belt 320 to form an integral one-piece belt and strap support for the immobilizing splint 100. This provides the maximum amount of support strength for holding up the splint, i.e., it can support a stronger load than the VELCRO® hook and loop connections. Further, since it comes with its own belt 320, it can be used by patients who normally do not wear their own belt. For example, it can be for women who wear dresses or anyone wearing pajamas, since the splint must be worn 24/7.

Figures 7A, 7B:
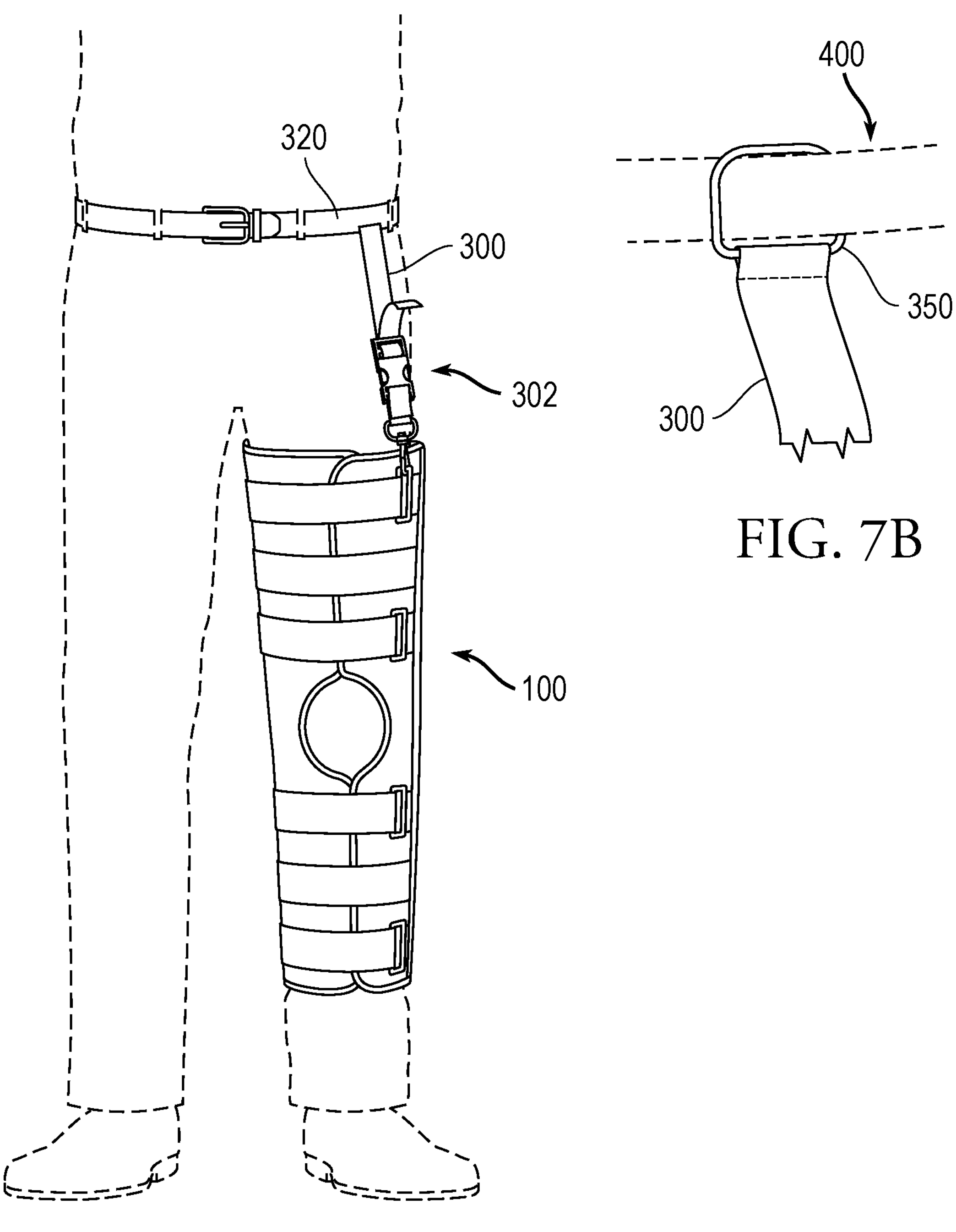

As shown in FIG. 7B, a loop 350, which can be oblong or a circular ring made of plastic or metal, can be sewn to the end of the strap 300. Then the user's own belt 400 or an auxiliary belt 320 can pass through it. This provides even more flexibility for the invention.

While the present invention has been particularly shown and described with reference to preferred embodiments thereof; it will be understood by those skilled in the art that various changes in form and details may be made therein without departing from the spirit and scope of the invention, and that the embodiments are merely illustrative of the invention, which is limited only by the appended claims. In particular, the foregoing detailed description illustrates the invention by way of example and not by way of limitation. The VELCRO® hook and loop strips, buckle clasps and loops can be interchanged as desired. Nevertheless, the description enables one skilled in the art to make and use the present invention, and describes several embodiments, adaptations, variations, and method of use of the present invention.

What is claimed is:

1. A support strap assembly for a one-piece knee immobilizing splint with a segment along a length of the splint located at indents formed in a perimeter of the splint that separate upper and lower portions of the splint and are adapted to receive a knee of a wearer, comprising:

a strap with a first end and a second end;

a first loop configured to be attached to the splint only at an upper part of the splint;

a second loop attached to the second end of the strap;

a hook connecting the second loop to the first loop; and a connection assembly at the first end of the strap, said connection assembly being adapted to adjustably connect to a belt worn by the wearer of the splint by being looped over the belt, the connection assembly comprising a first hook-and-loop fastener of a certain length on one side of the strap toward the first end thereof and a second hook-and-loop fastener longer than the first on the same side of the strap and longitudinally centered toward a longitudinal middle of the strap, and whereby the first end of the strap is adapted to be passed over the belt of the wearer and the first and second hook-and-loop fasteners brought into contact and fixed at variable distances with respect to each other so as to establish a certain distance from the belt to the upper part of the splint, whereby the splint is held such that the knee of the wearer is at the knee segment of the splint and the splint is prevented from sliding down the leg of the wearer while standing or walking; and an adjustable buckle clasp assembly located along the strap between the second hook-and-loop fastener and the second end of the strap to connect the second end to the hook.

2. The support strap assembly of claim 1 wherein the adjustable buckle clasp assembly has a first end connected to a portion of the strap extending toward the belt and a second end of the buckle clasp assembly connected to to the hook.

3. The support strap assembly of claim 2 further including a short strap connecting the second end of the buckle clasp assembly to the hook, whereby pulling on the second send of the strap shortens the distance between the belt and the splint.

* * * * *